United States Patent [19]

Frick

[11] 3,995,846
[45] Dec. 7, 1976

[54] MEANS SUPPORTING AN EXTREMITY OF THE BODY DURING THE APPLICATION OF A CAST

[76] Inventor: Mary A. LaRooka Frick, 1118 South 11th St., St. Charles, Ill. 60174

[22] Filed: Mar. 3, 1976

[21] Appl. No.: 663,574

[52] U.S. Cl. .............................. 269/328; 128/83
[51] Int. Cl.² .......................................... A61F 5/04
[58] Field of Search ............ 269/322, 328; 128/83, 128/133

[56] References Cited
UNITED STATES PATENTS

| | | | |
|---|---|---|---|
| 3,347,544 | 10/1967 | Uffenorde | 269/328 |
| 3,828,377 | 8/1974 | Fary | 269/328 |
| 3,908,643 | 9/1975 | Bliss | 128/83 |

*Primary Examiner*—Al Lawrence Smith
*Assistant Examiner*—Robert C. Watson
*Attorney, Agent, or Firm*—Hill, Gross, Simpson, Van Santen, Steadman, Chiara & Simpson

[57] ABSTRACT

An extremity support device which may be for a leg or arm to relieve strenuous physical handling of an extremity of a patient by medical personnel when treating the extremity of a patient, for example, as during the application of a cast thereto. The device is arranged to support a leg or arm at a select elevation and assist a physician in the application of a cast thereto, making it possible for one person to perform this operation. The device has an L-shaped support pad made from a foam material having a recess at the juncture of the legs of the L, for receiving the heel or elbow of the patient in elevated relation with respect to a bed or table upon which the patient may be lying or sitting. The bottom and side of the device opposite the recess may be provided with a non-skid material, enabling the device to be positioned on the bottom or end thereof so as to provide a non-moving, safe support while treatment is underway.

18 Claims, 6 Drawing Figures

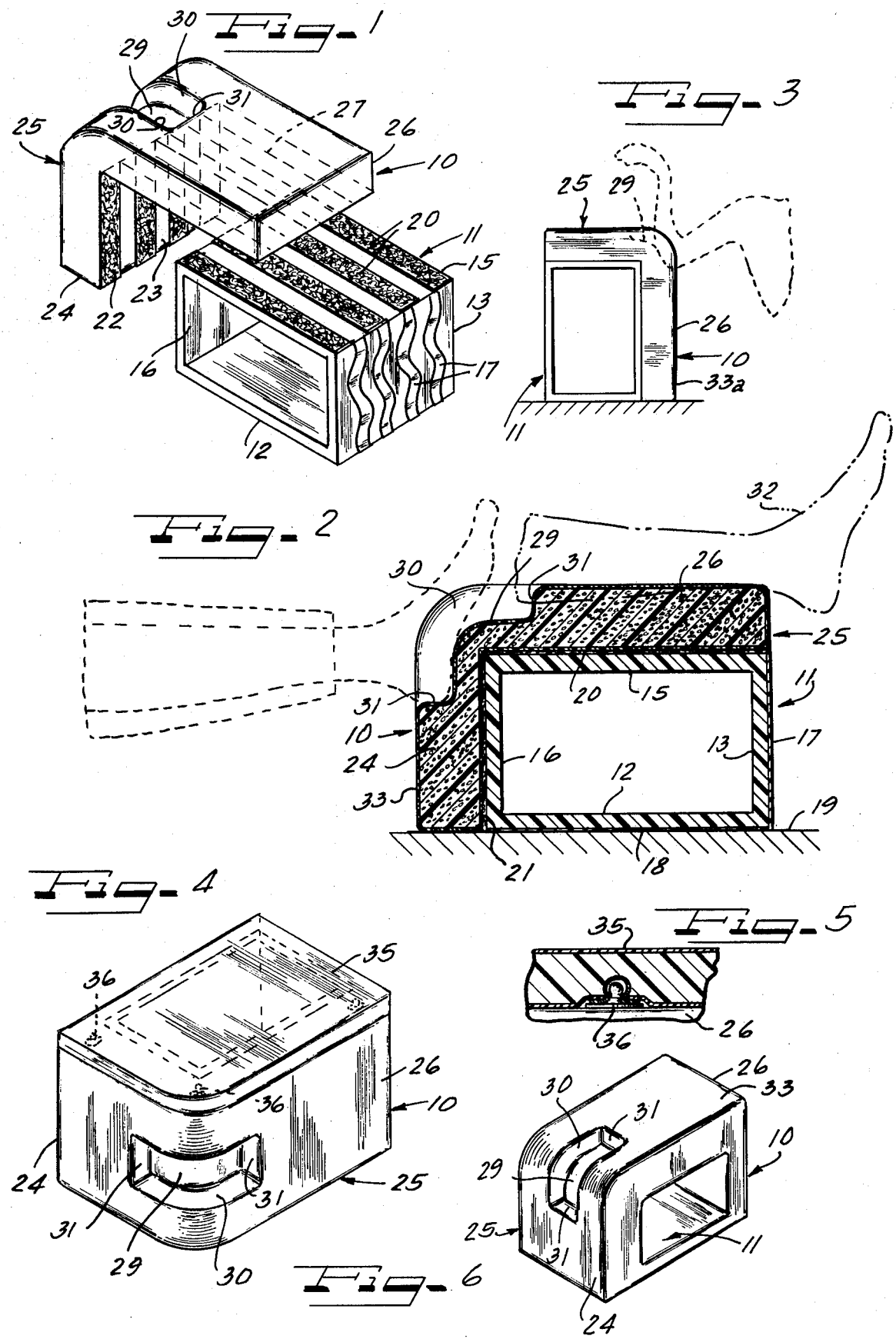

MEANS SUPPORTING AN EXTREMITY OF THE BODY DURING THE APPLICATION OF A CAST

FIELD OF THE INVENTION

This invention is in the field of orthopedics and somewhat more particularly to a device for supporting an injured leg or arm so as to enable a physician to treat such injured extremity.

PRIOR ART, BACKGROUND, SUMMARY AND ADVANTAGES OF INVENTION

U.S. Pat. No. 3,908,643 shows an adjustable limb support used while preparing a cast and while applying a cast to the foot or leg. The device shown by this patent is quite complicated and while adjustable, is not readily adapted for use while the patient is lying down and requires the foot and support structure to be wrapped with gauze or elastic material while the leg is maintained by the support in an adjusted fixed position.

Other forms of surgical supports for supporting the knee while operating on the knee are also known. Such supports are special supports and are not readily adaptable for the universal treatment of extremities, such as the application of a cast to the leg or arm.

U.S. Pat. Nos. 2,478,497; 2,911,657; 3,901,228 and 3,903,878 show various devices for supporting a leg or both legs of patients who are bedridden to prevent bed sores and the like from forming on the feet of such patients and to hold the bed covers above the feet to relieve the feet from pressure of the bed covers. However, these structures are not readily adaptable for use by a physician during treatment of an extremity, as in casting of legs or arms.

The device of my present invention overcomes the deficiencies of the prior art patents just mentioned by providing a device which protects and supports a limb, such as a leg or arm, at a select one of a plurality of elevations most convenient to the patient and physician during treatment of the limb, as in the application of a cast thereto and adds to the comfort of the patient during the treatment of an injured extremity, as during the application and drying of a cast and provides comfortable support for the limb after the treatment. The device is adapted to support an injured extremity so that a single person may treat the extremity, such as in applying a cast thereto, and dispense with assistance from other personnel. Further, the device of the invention avoids the strenuous efforts heretofore required to hold the extremity in proper position and allows a physician, for example, to simply apply a cast to the injured extremity and to then prop the extremity up on my device to enable the cast to properly dry.

Further, the device of the invention is readily storable at a convenient location, for example, in an emergency room or a physician's offices so as to be readily available and avoids the necessity of locating makeshift supports, such as pillows or the like presently used.

The advantages of the present invention, therefore, include that it provides a convenient non-moving, safe support while treatment is underway and relieves the patient from strain and pain and enables a physician to treat an extremity and apply a cast thereto in a fast and efficient manner without requiring assistance from other medical personnel.

A further advantage of the invention is that the device may support an extremity or limb at one of a plurality of elevations most convenient to the patient and/or physician during the treatment and application of a cast thereto.

A further advantage of the invention is that the device may support the limb in an elevated position with only limited contact between the device and the limb, thereby allowing air to circulate around the cast and aid in the drying process.

A still further advantage of the present invention is that the device may support a limb at a proper height for treatment, as during application of ice or the like to an injured limb and also support the pretreated limb at a proper height so as to avoid swelling and poor circulation of the limb, which frequently occurs during the application of a cast.

Another advantage of the invention is that the device may be readily adapted for use to persons of various heights, including a child, for the treatment of an injured extremity, for example application of a cast to the leg or arm.

Other objects, features and advantages of the invention will be readily apparent from the following description of certain preferred embodiments thereof, taken in conjunction with the accompanying drawings, although variations and modifications may be effected without departing from the spirit and scope of the novel concepts of the disclosure.

DESCRIPTION OF THE DRAWINGS

FIG. 1 is an exploded somewhat isometric view of a device constructed in accordance with the principles of the present invention;

FIG. 2 is a longitudinal sectional view taken through the device shown in FIG. 1;

FIG. 3 is a side view of the device showing the device positioned on one end, for supporting an extremity of the body while applying a cast thereto;

FIG. 4 is a generally isometric view of the device, showing a closure member detachably secured to a side of the device and adapting the device to form a support for an extremity at another elevation;

FIG. 5 is a partial fragmentary sectional view taken through a portion of the device and illustrating the use of a snap fastener for detachably connecting the closure member to a supporting framework for the device; and FIG. 6 is an isometric view of the device showing the device supported on its bottom with a rearwardly and upwardly facing recess therein for receiving a heel of a leg or an elbow of an arm.

DESCRIPTION OF PREFERRED EMBODIMENTS OF INVENTION

In the embodiment of the invention illustrated in FIGS. 1, 2, 3 and 6 of the drawings, I have shown an extremity support device 10 including an open rectangular framework 11 which may be made from wood, metal, plastic or other suitably rigid material and which has a bottom wall 12, rear end wall 13, a top wall 15 and a front end wall 16 parallel to the end wall 13. The size of the framework 11 may be varied as desired and a typical or convenient size useful for the general populace is about 15 × 9¼ × 9¼ inches. The thickness of the framework will depend upon the strength of the material used and generally a thickness of about ¾ inch is sufficient.

The end wall 13 may have a non-skid material 17 thereon, which may extend across the entire wall, or may be in the form of strips of a generally zig-zag form, as shown in FIG. 1, to increase the ability of the non-skid material to hold the device from slipping when placed on such end, generally in the position shown in FIG. 3. The bottom wall 12 may have similar non-skid material in the form of strips 18 extending therealong to prevent the device from slipping along a table 19 (FIG. 2) when the device 10 is positioned on the bottom thereof.

The non-skid material may be rubber, one of the well-known substitutes for rubber, or any other material which will provide good coefficient of friction to the bottom and end wall of the framework, enabling the device 10 to readily remain in position on a table or other support structure, and prevent slipping or sliding of the device during usage.

The top wall 15 may have strips 20 of Velcro (a registered trademark for nylon fasteners) or any other means commonly used to detachably attach one member to another, and retain the two members in attached relation with respect to each other unless intentionally separated. In some instances, it may be desirable to use snap fasteners or other selectively detachable fastening or securement means in place of Velcro strips. The end wall 16 may have similar flexible fastener strips 21, forming continuations of the strips 20, and extending therealong and registrable with Velcro strips 22 secured to an inner wall 23 of a leg 24 of a support pad 25.

The support pad 25 is generally L-shaped in side elevation and is relatively thick. The actual thickness dimensions may vary as desired and a convenient thickness is about 3 to 4 inches. The support pad 25 includes a relatively short leg 24 and a perpendicular relatively long leg 26, adapted to extend parallel to the top wall 15. The leg 26 may have Velcro strips 27 extending therealong for registry with the Velcro strips 20 for releasably anchoring the support pad 25 to the framework 11 and securely holding the support pad 25 to such framework.

The support pad 25 may be molded from a soft, lightweight material, such as foam rubber, urethane foam, Ethafoam (a registered trademark for foamed plastic material), or any other suitable material, to provide a soft but firm support for the injured extremity. The support pad 25 is provided with a recess 29 formed therein at the juncture of the legs 24 and 26. The recess 29 is shown as extending partially along the leg 26 and along the leg 24 and as having rounded upper and lower inner ends, which may generally conform to the heel and the adjoining part of the arch of the foot of a patient or the elbow when the device is resting on its bottom or end, as shown in FIGS. 2 and 3. The recess 29 has side walls 30 spaced a sufficient distance apart to fit the average heel or elbow of a patient being treated and prevent the extremity under treatment from freely moving. The recess 29 also has end walls 31 forming support surfaces for the heel or elbow. The recess is so formed as to support a limb at a relatively low elevation when the framework 11 is positioned on the bottom 12 and at a higher elevation when the framework is supported on the end 13.

A still different elevation of a limb may be attained by positioning the device 10 on the bottom thereof and placing a limb on the top of the support pad 25 for certain cast applying applications. This elevation is particularly useful for supporting a limb during the application of a walking cast to the foot. The leg and foot being in position for the application of a walking cast is shown by broken lines in FIG. 2 and indicated by reference numeral 32.

The manner in which the support pad 25 is attached to the framework 11 depends upon the material from which the support pad and framework are made, and in some instances, snap fasteners, screws or other securement means may be used in place of Velcro strips.

The support pad 25 may be covered by a soft, wear-resistant and washable material, such as Naugahyde (a registered trademark for plastic such as vinyl and/or rubber-coated fabrics generally used in upholstery), or any other suitable long-wearing, readily cleanable material and is indicated generally by reference numeral 33 in FIGS. 3 and 6. The support pad may also be provided with an outer cover of a disposable material 33a (FIG. 2) as of paper or gauze, or a sterilizable and washable material, such as vinyl or the like.

An additional limb supporting elevation may be attained by providing a side panel or cover 35 for the framework 11 and which generally conforms to the bottom and one side of the framework and to the form of the exterior portions of the support pad 25 (FIG. 4). The side panel 35 may be detachably secured to the side of the support pad by snap fasteners 36 as shown in FIG. 5, or by Velcro strips or any other suitable securing means. The injured limb, when placed on the side panel 35, may thus be supported at a still different elevation so as to accommodate the limb of a child or small adult. The thickness of the side panel or cover 35 may vary as required for a particular individual and such side panel may be in the form of a foam pad (having a construction essentially identical to that of support pad 25), which may or may not be covered with Naugahyde to support an arm or leg at the proper height for applying a cast thereto and to also support an arm or leg above a table while the cast is drying. While snap fasteners may be used to attach the side panel 35 to one side of the support, Velcro strips may also be used, if desired, or the side panel may be permanently attached to the support pad 25 or framework 11.

It may be seen from the foregoing that the device provided by the invention may be used for supporting the leg during the application of a cylinder cast, a long leg cast, a short leg cast, or during the application of a walking cast. The device may also support the arm for similar casts. The device may also form a support after the casting is finished to accommodate the circulation of air around the cast and the drying of the cast and enables a physician to apply a cast without help in holding the leg and leaves the nursing help free to work with the casting materials. Further, the device may also form a support before casting, as during the application of heat or ice to an injured limb for reducing the swelling thereof. The device may also be used in treating other injuries, such as burns or the like, since, depending on the injured area, a major portion of the limb is free of the support device so that contact with the injured area is either not required or at least minimized.

The device may be positioned to support the leg or arm at one of a plurality of select elevations by merely turning the device to rest on the bottom or the end wall or turning the device to rest on the side thereof. In addition, a side panel may be attached to one side of the device to provide a still different supporting elevation.

As is apparent from the foregoing specification, the invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the heretoappended claims.

I claim as my invention:

1. An extremity support device for extremities of the body to assist a physician in treating the extremity, comprising:
   a rigid framework having a bottom wall of a given dimension and an end wall of a dimension different from said given dimension, said walls being adapted to contact a support surface;
   a support pad attached to at least one wall of said framework;
   said support pad having a recess therein formed to fit a portion of an extremity of a patient and support the extremity in an elevated position;
   said bottom and end walls having a non-skid material thereon;
   said bottom and end walls of said framework being so arranged as to support the extremity at one elevation when resting on the bottom wall and at another elevation when resting on the end wall.

2. The extremity support device of claim 1, wherein the framework is also constructed to rest on a side thereof and provide a support surface at a different elevation than when resting on the bottom or end walls thereof.

3. The extremity support device of claim 1, wherein the framework is open to both sides and a side panel member is provided to close an open portion thereof and provide a support surface at an elevation different from the elevation when the device is resting on said bottom or end walls.

4. The extremity support device of claim 1, including an open framework defining the bottom and one side of the device, a relatively thick pad formed of foam material and generally L-shaped in side elevation, formed to conform to one end and the top of the framework, said pad having the recesses formed in the foam at the juncture of the legs of the L so as to fit a portion of a limb, said recesses being accessible as a support surface when the extremity support device is positioned on the bottom or side thereof.

5. The extremity support device of claim 4, wherein the bottom and one side of the open framework are provided with a non-skid material to prevent the support device from slipping.

6. The extremity support device of claim 4, wherein the non-skid material is a rubber-like material in the form of strips.

7. The extremity support device of claim 4, wherein the relatively thick pad of foam generally L-shaped in side elevation is detachably secured to the open framework by spaced flexible securement strips.

8. The extremity support device of claim 4, wherein the relatively thick pad of generally L-shape in side elevation is detachably secured to the open framework by snap fasteners.

9. The extremity support device of claim 4, wherein a side panel is attached to one side of the open framework and defines a support surface for an extremity of the body at a desired elevation when the device is positioned on the side opposite said side panel.

10. The extremity support device of claim 4, wherein at least the support pad is covered by a soft, wear-resistant material.

11. The extremity support of claim 10, wherein the soft, wear-resistant material is a plastic-coated fabric.

12. The extremity support device of claim 4, wherein the relatively thick pad of generally L-shape in side elevation has flexible securement strips extending along each leg of the L facing the open framework, and the open framework has similar flexible securement strips extending along the top and one end thereof in registry with the securement strips on the legs of the pad so as to detachably secure the pad to the open framework.

13. The extremity support device of claim 4, wherein the recess receives the heel of a foot when the device is positioned on the bottom or end thereof, and strips of a non-skid material are provided along the bottom and end of the open framework.

14. The extremity support device of claim 13, wherein the non-skid strips are of a rubber-like material.

15. The extremity support device of claim 12, wherein a side panel member is provided to fit on one side of the open framework to provide a third elevation for supporting an extremity of the body when the support device is positioned on its side.

16. The extremity support device of claim 12, wherein the side panel member includes a detachable securement means for attaching said member to the pad on the framework.

17. The extremity support device of claim 4, wherein at least the support pad has an outer covering formed of a disposable material.

18. The extremity support device of claim 4, wherein at least the support pad has an outer covering formed of a sterilizable material.

* * * * *